United States Patent [19]

Van der Knaap

[11] Patent Number: Plant 6,780

[45] Date of Patent: May 2, 1989

[54] CHRYSANTHEMUM PLANT NAMED RIOHACHA

[75] Inventor: Jacques C. M. Van der Knaap, De Lier, Netherlands

[73] Assignee: Fides Beheer B.V., De Lier, Netherlands

[21] Appl. No.: 144,028

[22] Filed: Jan. 14, 1988

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Riohacha, having flat capitulum form and single capitulum type. The ray florets are bicolored, being comprised of yellow and red, presenting a very attractive appearance.

1 Drawing Sheet

1

The present invention comprises a new and distinct cultivar of *Chrysanthemum morifolium,* hereinafter referred to by the cultivar name Riohacha.

Riohacha is a product of a planned breeding program which had the objective of creating new Chrysanthemum cultivars with single capitulum type, bicolored ray florets, nine (9) week response, and the ability to produce commercially acceptable quality in year around cut mum programs. Such traits in combination were not present or needed improvement in previously available commercial cultivars.

Riohacha was originated from a hybridization made by applicant in a controlled breeding program in De Lier, Holland in 1984. The female parent was Harlekijn, disclosed in a pending plant patent application of applicant. The male parent of Riohacha was Impala, also disclosed in a pending plant patent application of applicant.

Riohacha was discovered and selected as one flowering plant within the progeny of the stated parentage by Jacques C. M. Van der Knaap in June 1984 in a controlled environment in De Lier, Holland.

The first act of asexual reproduction of Riohacha was accomplished when vegetative cuttings were taken from the initial selection in August 1984 in a controlled environment in De Lier, Holland by a technician working under formulations established and supervised by Jacques C. M. Van der Knaap. Horticultural examination of selected units initiated in March 1985 has demonstrted that the combination of characteristics as herein disclosed for Riohacha are firmly fixed and are retained through successive generations of asexual reproduction.

Riohacha has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Riohacha, which in combination distinguish this Chrysanthemum as new and distinct cultivar:

1. Flat capitulum form.
2. Single capitulum type.

2

3. Bicolored (yellow-red) ray florets.
4. Diameter across the face of the capitulum is 60–70 mm.
5. Yellow-green (immature) to yellow (mature) disc florets.

Of the many commercial cultivars known to the present inventor, the most similar in comparison to Riohacha is Hofnar, a dark bronze mutation of Harlekijn. In comparison to Hofnar, Riohacha has smaller flowers, shorter ray florets, a visibly different ratio of the colors yellow and red in the ray florets, and longer response time. The capitulum form, capitulum type, and disc floret color are similar to those same characteristics of Hofnar.

The accompanying photographic drawing shows in perspective view typical inflorescence and foliage characteristics of Riohacha, with colors being as nearly true as possible with illustrations of this type.

In the following description, color references are made to The Royal Horticultural Society Colour Chart. The color values were determined between 11:00–12:00 a.m. in September 1985 under natural daylight at De Lier, Holland.

Classification:

*Botanical.—Chrysanthemum morifolium,* Ramat., cv. Riohacha.

*Commercial*—Cut daisy spray.

INFLORESCENCE

A. Capitulum:

*Form.*—Flat.

*Type.*—Daisy.

*Diameter across face.*—60–70 mm.

B. Corolla of ray florets:

*Color (general tonality from a distance of three meters).*—Red-yellow.

*Color (upper surface).*—5B mixed with 171A.

C. Corolla of disc florets:

*Color (mature).*—Yellow.

*Color (immature).*—Green.

D. Reproductive organs:

*Androecium.*—Present only in disc florets; numerous.

*Gynoecium.*—Present in both disc and ray florets; numerous.

PLANT

A. General appearance:

*Height.*—90 cm.

B. Foliage:

*Color* (*upper surface*).—147A.

*Color* (*upper surface*).—147B.

I claim:

1. A new and distinct cultivar of Chrysanthemum plant named Riohacha, as illustrated and described, and parts thereof.

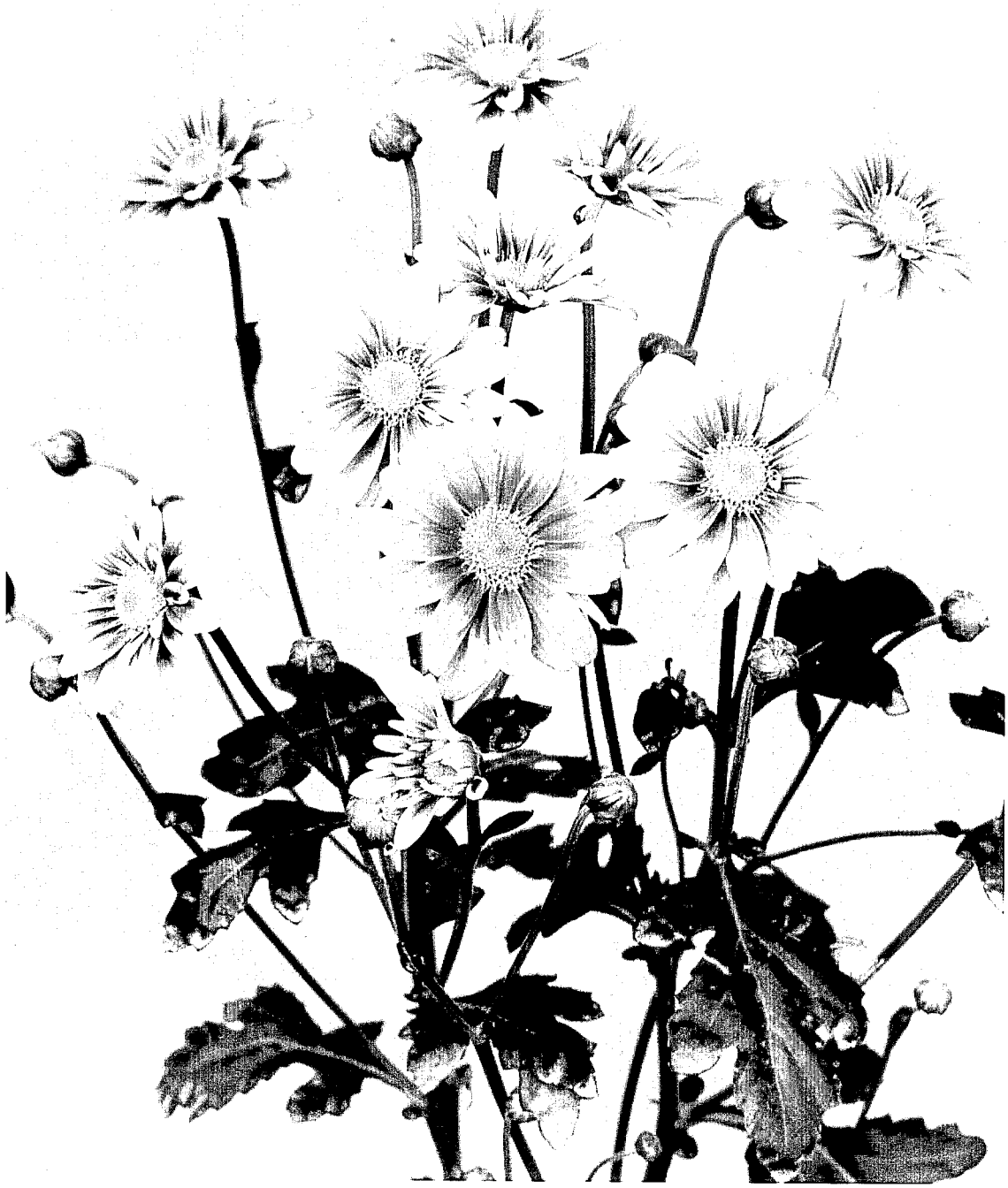

* * * * *